United States Patent [19]

Nicolson et al.

[11] Patent Number: 4,859,581

[45] Date of Patent: Aug. 22, 1989

[54] ENDOGLYCOSIDASE ASSAY

[75] Inventors: Garth L. Nicolson, Kingwood; Motowo Nakajima, Houston; Tatsuro Irimura, Bellaire, all of Tex.

[73] Assignee: Board of Regents, The University of Texas System, Austin, Tex.

[21] Appl. No.: 12,860

[22] Filed: Feb. 20, 1987

Related U.S. Application Data

[63] Continuation-in-part of Ser. No. 839,890, Mar. 10, 1986.

[51] Int. Cl.[4] .............................................. C12Q 1/00
[52] U.S. Cl. ......................................... 435/4; 435/7; 435/13
[58] Field of Search ...................... 435/13, 18, 19, 4, 7

[56] References Cited

U.S. PATENT DOCUMENTS 4,385,046  5/1983  Milbrath et al. ...................... 424/9

OTHER PUBLICATIONS

Vora–Chem. Abst., vol. 102 (1985), p. 145, 109b.
Nakajima et al., *J. Biol. Chem.* (1984), 259: 2283–2290.
Irimura et al., *Analyt. Biochem.* (1983), 130: 461–468.
Irimura et al., *Proc. Am. Soc. Cancer Res.* (1983), 24: 37, Abstr. 144.
Nakajima et al., *Science* (1983), 220: 611–613.
Vlodavsky et al., *Cancer Res.* (1983), 43: 2704–2711.
Kramer et al., *J. Biol. Chem.* (1982), 257: 2678–2686.
Nicolson, *Biochim. Biophys. Acta* (1982), 695: 113–176.
Nicolson, *J. Histochem. and Cytochem.* (1982), 30: 214–220.
Oosta et al., *J. Biol. Chem.* (1982), 257: 11249–11255.
Kanwar et al., *J. Cell. Biol.* (1980), 86: 688–693.
Oldberg et al., *Bio. Chem.* (1980), 19: 5755–5762.
Iverius, *Biochem. J.* (1971), 124: 677–683.
Nakajima et al., Cancer Metastasis: Experimental and Clinical Strategies (1985).

*Primary Examiner*—Sam Rosen
*Attorney, Agent, or Firm*—Arnold, White & Durkee

[57] ABSTRACT

A solid phase substrate which yields soluble labeled products upon hydrolysis by a glycosaminoglycan endoglycosidase and methods of producing said substrate are comprised in the present invention. The solid phase substrate comprises glycosaminoglycan bearing labeled substances bound to amino groups. The labeled glycosaminoglycan substrate is reductively aminated at its reducing terminal end to produce an amine-terminus. The substrate is further coupled to an amino-reactive solid matrix through its amine-terminus.

A method of producing the solid phase substrate comprises the steps of: at least partially N-desulfating or N-deacylating a glycosaminoglycan; labeling at least partially N-deacylated or N-desulfated glycosaminoglycan with a substance yielding detectable signals to produce labeled glycosaminoglycan; completely N-acylating the labeled glycosaminoglycan with acyl anhydride or acyl halide; reductively aminating a reducing terminal end of said labeled glycosaminoglycan to produce labeled amine-terminal glycosaminoglycan; and coupling, through its terminal amine, the labeled amine-terminal glycosaminoglycan to an amino-reactive solid phase support to produce the solid phase substrate.

The solid phase substrate is usable to detect metastatic tumors by measurement of serum heparanase levels. The potential metastases of a tumor may also be determined by its heparanase levels.

22 Claims, 5 Drawing Sheets

ENDOGLYCOSIDASE ASSAY

CROSS REFERENCES TO RELATED APPLICATION

This application is a continuation-in-part of U.S. patent application Ser. No. 839,890 filed March 10, 1986.

BACKGROUND OF THE INVENTION

The present invention relates to an assay for endoglycosidase enzymic activity and a labeled substrate for use in such an assay. The assay of the present invention is viewed as useful for the detection of cancerous malignancies.

A class of biological substances called the proteoglycans form the ground substance in the extracellular matrix of connective tissues. These proteoglycans are polyanionic substances of high molecular weight and contain many different types of heteropolysaccharide side chains covalently linked to a polypeptide backbone. These proteoglycans may contain over 95% carbohydrates. The polysaccharide groups of the proteoglycans were formerly called mucopolysaccharides but now are preferably termed glycosaminoglycans since all contain derivatives of glucosamine or galactosamine.

A variety of enzymes may be involved in the normal metabolic degradation of proteoglycans. Initial proteoglycan degradation often involves proteolysis to separate or digest protein components. Such proteolysis results in the production of glycosaminoglycans. The glycosaminoglycans in turn are subject to glycosaminoglycan endoglycosidase enzymic action which produces smaller glycosaminoglycan fragments. The glycosaminoglycans or fragments thereof are subject to glycosaminoglycan exoglycosidase enzymic action which produces monosaccharides from the non-reducing ends of glycosaminoglycans.

An increasing interest in the endoglycosidases has arisen in recent years because of a possible relationship of these enzymes with tumor invasiveness and tumor metastatic activity. Nicolson (1982, Biochem. Biophys. Acta. V 695, pp 113-176) reviewed a variety of oligosaccharide-degrading enzymes (pp 141-142) reported to be of interest in malignant disease. Nicolson (1982, J. Histochem. & Cytochem. V 30, pp 214-220) described a proposed mechanism for tumor cell invasion of endothelial cell basal lamina and a related production of degradation products from proteins and glycosaminoglycans. Kramer et al. (1982, J. Biol. Chem. V 257, pp 2678-2686) reported a tumor-derived glycosidase capable of cleaving specifically glycosaminoglycans and releasing heparan sulfate-rich fragments.

Irimura et al. (1983, Analyt. Biochem. V 30, pp 461-468) describe high-speed gel-permeation chromatography of glycosaminoglycans. Heparan sulfate degrading activity of melanoma cells was measured by using this chromatographic procedure. Nakajima et al. (1983, Science, V 220, pp 611-613) described a relationship of metastatic activity and heparan sulfate degrading activity in melanoma cell lines. The disappearance of higher molecular weight heparan sulfate was followed by polyacrylamide gel electrophoresis, staining and densitometry.

Vlodavsky et al. (1983, Cancer Res. V 43, pp 2704-2711) described the degradation by two T-lymphoma cell lines of $^{35}S$ labeled proteoglycans from confluent endothelial cells. The highly metastatic line had much higher $^{35}S$ liberating activity than did the low metastatic line.

Irimura et al. (1983, Proc. Am. Soc. Cancer Res. V 24, p 37, abstract 144), using high performance liquid chromatography, describe heparan sulfate degradative enzyme activity of melanoma cells. Nakajima et al (1984, J. Biol. Chem. V 259, pp 2283-2290) describe characterizations of metastatic melanoma heparanase. High speed gel permeation chromatography and chemical analyses were used in a description of functional substrates and products formed.

The background described herein involves an interest in convenient, accurate and reproducible endoglycosidase assays, particularly since endoglycosidases may play critical roles in the establishment of tumor metastases.

The ability of tumor cells to invade host tissues and metastasize to distant, often specific organ sites, is one of their most important properties. Metastasis formation occurs via a complex series of unique interactions between tumor cells and normal host tissues and cells. These processes involve several discrete and selective steps such as: invasion of surrounding tissues, penetration of lymphatics of blood vessels and transport in lymph or blood, or dissemination into a serous cavity, arrest and invasion at distant sites, and survival and growth to form secondary lesions.

Basement membranes are continuous sheets of extracellular matrix composed of collagenous and non-collagenous proteins and proteoglycans that separate parenchymal cells from underlying interstitial connective tissue. They have characteristic permeabilities and play a role in maintaining tissue architecture. Metastasizing tumor cells must penetrate epithelial and endothelial basement membranes during invasion and metastasis, and the penetration and destruction of basement membranes by invasive tumor cells has been observed using electron microscopy. Since basement membranes are rigid structures formed from unique sets of macromolecules, including type IV collagen, laminin, heparan sulfate (HS), proteoglycan and fibronectin, the successful penetration of a basement membrane barrier probably requires the active participation of more than one tumor cell-associated enzyme.

Due to its unique physical and chemical properties such as its polyanionic character and barrier properties against macromolecules (Kanwar et al., 1980 J. Cell. Biol. V 86, pp 688-693), heparan sulfate (HS) is an important structural component of basement membranes. HS binds to fibronectin, laminin and type IV collagen, and these molecules have been collectively observed in the basal lamina using antibodies raised against each component. HS may be involved in basal lamina matrix assembly by promoting the interactions of collagenous and non-collagenous protein components while protecting them against proteolytic attack. Thus, the destruction of HS proteoglycan barrier could be important in basement membrane invasion by tumor cells.

The interactions between malignant cells and vascular endothelium have been studied using monolayers of cultured vascular endothelial cells that synthesize an extracellular matrix resembling a basement membrane. With this model, it has been found that metastatic B16 melanoma cells degrade matrix glycoproteins, such as fibronectin, and matrix sulfated glycosaminoglycans, such as heparan sulfate. Since heparan sulfate was released in solution as fragments approximately one-third their original size, it has been proposed that metastatic tumor cells characteristically have a heparan sulfate endoglycosidase.

The relation between metastatic properties and the ability of five B16 melanoma sublines of various implantation and invasion characteristics to enzymatically degrade subendothelial extracellular matrix indicated that highly invasive and metastatic B16 sublines degraded sulfated glycosaminoglycans faster than did sublines of lower metastatic potential (Nakajima et al., (1983), Science V 220, p 611), and intact B16 cells (or their cell-free homogenates) with a high potential for lung colonization also degraded purified heparan sulfate at higher rates than did B16 cells with a poor potential for lung colonization (ibid). The abilities of B16 cells to degrade HS from various origins and other purified glycosaminoglycans (heparin, chondroitin 4-sulfate, chondroitin 6-sulfate, dermatan sulfate, keratan sulfate, and hyaluronic acid) has been studied. In order to analyze glycosaminoglycan degradation products, an analytic procedure was developed using high-speed gel permeation chromatography (Irimura et al., (1983) Anal. Biochem. V 130, p 161; Nakajima et al., (1984) J. Biol. Chem. V 259, p 2283). HS metabolically labeled with [$^{35}$S]sulfate was purified from basement membrane producing EHS sarcoma and PYS-2 carcinoma cells, and subendothelial matrices of bovine aortic endothelial (BAE) and corneal endothelial (BCE) cells (ibid). HS molecules purified from bovine lung and other glycosaminoglycans were labeled with tritium at their reducing termini using NaB[$^3$H]$_4$. These labeled glycosaminoglycans were incubated with B16 cell extracts in the absence or presence of D-saccharic acid 1,4-lactone, a potent exo-beta-glucuronidase inhibitor, and degradation fragments were analyzed by high-speed gel permeation chromatography. HS isolated from the various origins described above were all degraded into fragments of characteristic molecular weight, in contrast to hyaluronic acid, chondroitin 6-sulfate, chondroitin 4-sulfate, dermatan sulfate, keratan sulfate, and heparin, which were essentially undegraded. Heparin, but not other glycosaminoglycans, inhibited HS degradation. The time dependence of HS degradation into particular molecular weight fragments indicated that melanoma heparanase cleaves HS at specific intrachain sites (ibid). In order to determine specific HS cleavage points, the newly formed reducing termini of HS fragments were investigated by: labeling with NaB[$^3$H]$_4$; hydrolysis to monosaccharides; and analysis of these saccharides by paper chromatography. Since $^3$H-reduced terminal monosaccharides from HS fragments were overwhelmingly (>90%) L-gulonic acid, the HS-degrading enzyme responsible was an endoglucuronidase (heparanase).

HS-degrading endoglucuronidases have been found in various tissues, such as human skin fibroblasts, rat liver cells, human placenta, and human platelets. HS-degrading endoglucuronidases in mammalian cells were reported previously by other investigators to be "heparitinases" to indicate heparitin sulfate (heparan sulfate)-specific endoglycosidase. However, heparitinase originally was used to designate an elimination enzyme (EC 4.2.2.8) in *Flavobacterium heparinum*, and this enzyme cleaves non-sulfate and monosulfated 2-acetoamido-2-deoxy-alpha-D-glucosyl-D-hexuronic acid linkages of HS. Since HS-specific endoglycosidases in mammalian cells are endoglucuronidases, except for one found in skin fibroblasts, it was proposed that mammalian cell endoglucuronidases capable of degrading HS should be called "heparanases", consistent with the currently used term "heparan sulfate".

Glycosaminoglycan endoglycosidaes have been assayed for enzyme activity by some other means. For example, Oldberg et al. (1980, Biochem. V 19, pp 5755-5762) described an assay for a platelet endoglycosidase which degraded heparin-like polysaccharide. This assay involved measuring a decreasing amount of $^3$H-heparan sulfate, the decrease being a function of endoglycosidase activity.

Endoglycosidase assays using solid-phase substrates were described by Iverius (1971, Biochem. J. V 124, pp 677-683) and Oosta et al. (1982, J. Biol. Chem. V 257, pp 11249-11255). Iverius coupled a variety of glycosaminoglycans to cyanogen bromide-activated Sepharose 4B beads. In one case the endoglycosidase hyluronidase was assayed for enzymic activity by incubation of the enzyme with chondroitin sulfate bound to Sepharose 4B. The enzyme activity was monitored by following the production of soluble uronic acid with a colorimetric assay procedure. Oosta et al. described an assay for heparitinase, an endoglycosidase from platelets which cleaves heparin and heparan sulfate.

The Oosta et al. system and assay comprised:
(1) Coupling heparin with N-succinimide 3-(4-hydroxylphenyl) propionate.
(2) Labeling the coupled heparin by incubation with Na$^{125}$I and chloramine-T.
(3) Coupling the $^{125}$I heparin to cyanogen bromide-activated beads of Sepharose 4B, and
(4) Incubating the endoglycosidase with the $^{125}$I-heparin coupled to Sepharose 4B beads and measuring solublized radioactivity.

In these two methods, glycosaminoglycans were crosslinked to agarose by the reaction of free amino groups of glycosaminoglycans and amino-reactive cyanogen bromide-activated agarose. Since glycosaminoglycans, such as heparin and heparan sulfate, have several free glucosamine amino groups, this type of crosslinking results in excessive covalent linkages between substrate molecules and agarose gel, resulting in a loss of susceptbility to endoglycosidases and nonlinear rates of degradation. Thus the most desirable solid-phase substrate for glycosaminoglycan endoglycosidase is glycosaminoglycan crosslinked to a solid support at one end of the molecule such as reducing terminal.

SUMMARY OF THE INVENTION

A solid phase substrate which yields soluble labeled products upon hydrolysis by a glycosaminoglycan endoglycosidase and methods of producing said substrate are comprised in the present invention. The solid phase substrate comprises glycosaminoglycan bearing labeled N-acetyl groups and being reductively aminated at its reducing terminal end to produce an amine-terminus. The substrate is further coupled to an amino-reactive solid matrix through its amine-terminus.

A method of producing the solid phase substrate comprises the steps of: at least partially N-desulfating or N-deacetylating a glycosaminoglycan; labeling at least partially N-deacetylated or N-desulfated glycosaminoglycan to produce labeled glycosaminoglycan; completely N-acylating the labeled ghycosaminoglycan with acyl anhydride or acyl halide; reductively aminating a reducing terminal end of said labeled glycosaminoglycan to produce labeled amine-terminal glycosaminoglycan; and coupling, through its terminal amine, the labeled amine-terminal glycosaminoglycan to an amine-reactive solid phase support to produce the solid matrix substrate.

The labeling may be accomplished by substitution on amino groups of the partially N-desulfated or N-deacetylated glycosaminoglycan of a substance yielding a detectable signal. This substance may be a radioisotopic label, a fluorescent label or an enzymatic label. A fluorescent label is preferred for ease of assay and a radioisotopic label for similarity to the natural glycosaminoglycan.

BRIEF DESCRIPTION OF PREFERRED EMBODIMENTS

Figure 1:
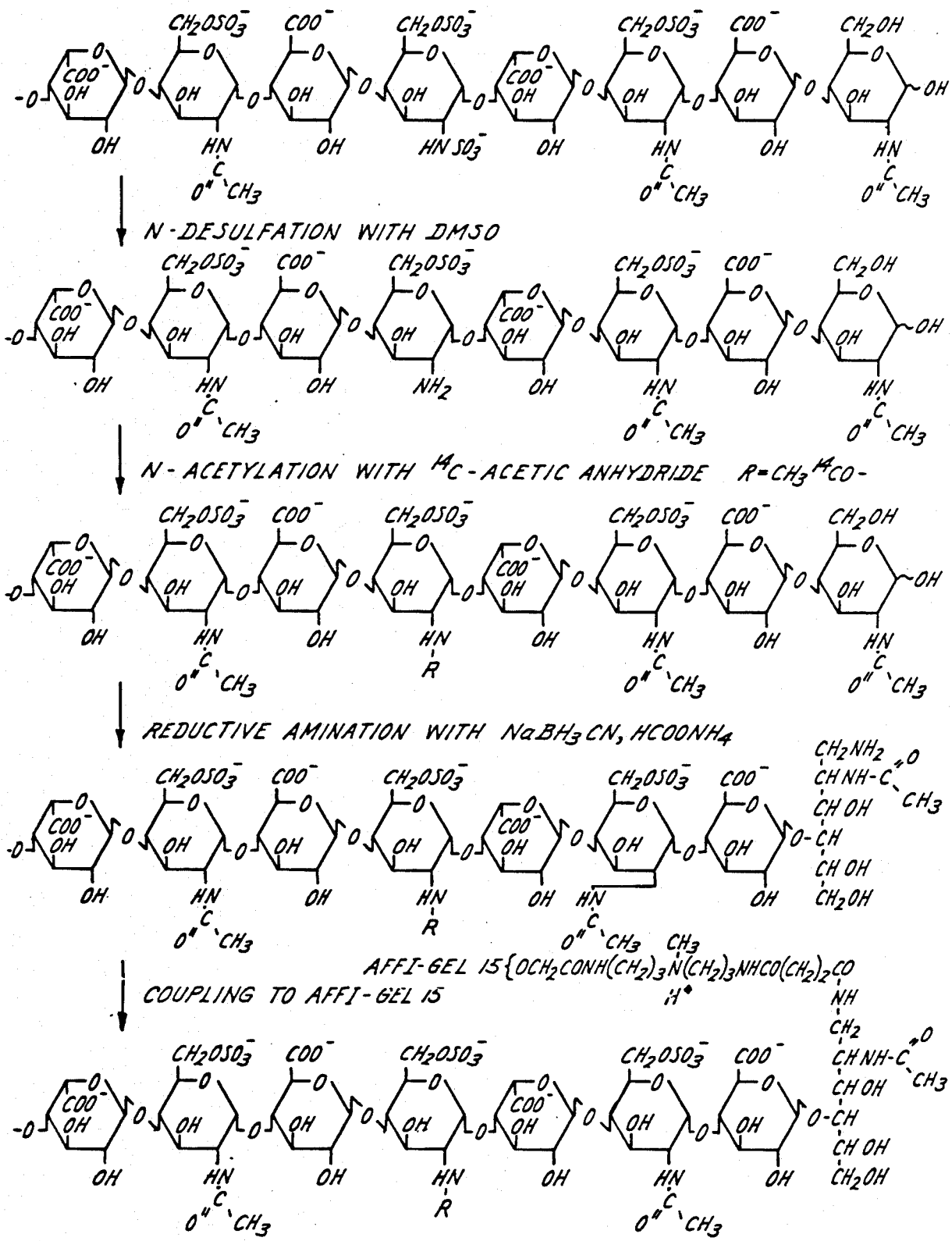
FIG. 1. Synthesis of a solid-phase heparanase substrate: Chemical modification and radiolabeling of HS and its coupling to amino-reactive agarose gel bead.

The present invention involves a new assay for glycosaminoglycan endoglycosidase activity, most preferably that of the heparan sulfate endoglycosidase termed "heparanase". This new assay describes using a solid phase substrate which yields soluble labeled products upon hydrolysis by a glycosaminoglycan endoglycosidase. The new assay also describes novel adaptations of this solid phase enzymatic assay to liquid-phase conditions. Immunoassays, such as those using antibodies raised to an glycosaminoglycan endoglycosidase such as heparan sulfate endoglycosidase, for example, are also described, which measure the enzyme.

This solid phase substrate comprises a glycosaminoglycan bearing radioisotopically labeled N-acyl groups. These labeled N-acyl groups are preferably $^3$H labeled or $^{14}$C labeled acetyl groups although other labeled acyl groups, such as formyl or propionyl groups may be used. The solid phase substrate of the present invention may comprise as the glycosaminoglycan: hyaluronic acid, chondroitin 4-sulfate, chondroitin 6-sulfate, dermatan sulfate, keratan sulfate, heparan sulfate, heparin, or combinations thereof. The use of particular glycosaminoglycans will allow assays for the enzymic activity of endoglycosidases having a substrate specificity for the particular glycosaminoglycan being used.

The amino-reactive solid matrix to which the amine-terminal labeled glycsaminoglycan may be bound may have many acceptable forms, both in the basic nature of the matrix and in the amine-reactive chemical site.

A preferable solid matrix is agarose-based, most preferably Sepharose or Sepharose derivatives in bead form (Pharmacia). Other solid matrices such as celluloses or polyacrylamides may be used provided that the have amine-reactive substituent functions for coupling.

It is well known that Sepharose beads may be activated with cyanogen bromide and then coupled to amine-bearing molecules such as heparin, other glycosaminoglycans or glycosaminoglycan derivatives. Cyanogen bromide mediated coupling, is a usable coupling method for practice of the present invention. Cyanogen bromide activated agarose or any other amine-reactive solid matrix may couple to more than one amine group of a glycosaminoglycan and glycosaminoglycan derivative with multiple amine functions. This multiple coupling to labeled glycosaminoglycans could lead to insensitive and/or inaccurate glycosaminoglycan endoglycosidase assays, since a single glycosidase-mediated hydrolytic event may not result in a soluble product, i.e., a product not linked to the solid matrix. Thus for the practice of the present invention, it is of importance that the labeled glycosaminoglycan derivative to be bound to a solid matrix has but a single primary amino-group.

While a variety of amine-reactive substituents are known to those skilled in the art, an N-hydroxy succinide ester is a preferable amine-reactive function bound to a solid matrix and is commercially available or readily synthesized. Such N-hydroxysuccinide esters couple to primary amine goups at a pH between about 6 and 9. Agarose may be activated by periodate oxidation to contain aldehyde functions. This aldehydic agarose may be reacted with labeled amine-terminal glycosaminoglycan and the linkage stabilized by reduction with sodium cyanoborohydride. (Perikh et al., Methods in Enzym. Vol XXXIV, p 81 Acad. Press (1974)). Other commonly used procedures which may be used to link amine-bearing labeled glycosaminoglycans to solid matrices include: using a carbodiimide and a carboxyl-bearing solid matrix; directly reacting the amine-bearing labeled glycosaminoglycan with a solid matrix bearing a bromoacetyl, diazonium or epoxy function.

The glycosaminoglycans generally have their amine functions either sulfated or acetylated. After at least partial N-desulfation or N-deacetylation, for example, the resultant primary amino groups on the glycosaminoglycan are available for labelling. Deacetylation may be accomplished by hydrazinolysis under conditions avoiding excessive alkalinity which could lead to hybrolysis of glucosaminyl linkages. Desulfation may be accomplished by formation of pyridinium salts of the glycosaminoglycan followed by solvolysis in dimethylsulfoxide. Amino group labeling is accomplished by reaction with a fluorescent compound such as fluorescein isothiocyanate, an enzyme such as alkaline phosphatase (and a bifunctional coupling agent) or with a radioisotopically labeled acyl anhydride or acyl halide. A label is then covalently attached to at least some of the free amine groups. Remaining free amine groups of the labeled glycosaminoglycan are then acylated, for example by acetic anhydride treatment. The acylated labeled glycosaminoglycan is then aminated at its reducing terminal. This amination is accomplished by incubation with an amine salt to form a Schiff base with the terminal and subsequent reduction to form a terminal amine.

Amino group labeling may be accomplished by coupling a measurable compound or active protein to at least a few of the amino groups. The measurable compound may be one of the many known to be highly absorbent of visible light or more preferably one which is fluorescent when excited by irradiation at particular wavelengths such as fluorescein as mentioned above. Labeling by attachment of enzymes (as alkaline phosphatase mentioned above) as active proteins to the partially N-desulfated or N-deacetylated glycosaminoglycan is also a possibility. Labeling by enzymes or measurable compounds having light absorbent or fluorescent structures, however, may involve sterically bulky substituents. Such sterically bulky substituents may, when substituted at too high a level, render glycosaminoglycan derivatives which are poor substrates for glycosaminoglycan endoglycosidases. In preliminary experiments, a partially N-desulfated heparan sulfate was coupled in a 1:1 ratio to fluoroscein isothiocyanate. This fluorescein labeled derivative was found to be a good substrate for melanoma heparanase. It is contemplated that up to a 10:1 ratio of fluorescein to HS may be produced and serve as a haparanase substrate.

One or a very few of these bulky substituents may not hinder substrate activity and result in good labeled substrates. Another potential problem with enzyme labels is that enzymes generally contain free amine groups which may bind to amine-reactive solid matrices. One preferred label for glycosaminoglycans is a radioisotopic label similar or identical in structure to naturally occuring N-substituents. While $^{35}$S-sulfate N-substituents could be utilized, $^{14}$C- or $^3$H-acetyl N-substituents are preferred as readily produced. Although the subsequently described substrates and procedures relate primarily to radioisotopic labeling there are largely applicable in principle to other labels, particularly fluorescent labels.

When N-radioisotopically labeled glycosaminoglycans are attached by a single bound at one end to a solid matrix, a solid phase substrate for a glycosaminoglycan endoglycosidase is created. As described elsewhere herein, this solid phase substrate yields soluble radioisotopically labeled substances as a function of glycosaminoglycan endoglycosidase enzymatic activity. An alternative manner of measuring this same activity would be to observe the disappearance of radioisotopic label bound to the solid matrix as a function of enzymatic activity. This type of measurement has the disadvantage of being a negative measurement and also that incubation supernatant would have to be carefully removed from residual solid matrix substrate.

In a broad sense, the solid phase substrate of the present invention is one which yields soluble products labeled with a detectable signal upon hydrolysis by a glycosaminoglycan endoglycosidase. This solid phase substrate comprises a glycosaminoglycan bearing a label which does not prevent hydrolysis of the labeled glycosaminoglycan by a glycosaminoglycan endoglycosidase. The labeled glycosaminoglycan is linked through a single end, preferably the reducing terminal end and by a single covalent linkage, to a solid matrix. The detectable signal may be radioisotopic, light absorbent, fluorescent or enzymatically active. The solid matrix is preferably hydrophilic and may include polymers such as cellulose, dextran, polyacrylates or their derivatives, alone or in combination. The substrate of the present invention may be soluble if a detectable label is present along with a tagging molecule. The tagging molecule may be used as a 'handle' for removal of a portion of attached glycosaminoglycan.

The labeling of at least partially desulfated or deacylated glycosaminoglycan is most preferably accomplished by treatment with 3H-acetic anhydride or $^{14}$C-acetic anhydride, although analogous acetyl halides, particularly chlorides or also alkyl bromides are contemplated as useful. In addition to other acyl functions such as formyl or propionyl, other coupling methods may be used in this labelling procedure.

The substrate of this invention may also be a liquid phase substrate with separation of the cleaved products from the uncleaved substrate occuring after the enzymatic reaction. In this scheme, a glycosaminoglycan such as heparan sulfate, for example, could be tagged at one end, preferably the reducing end, to another molecule. The glycosaminoglycan should be labeled at additional sites by other molecules such as $^{125}$I, fluorescein, enzymes, and the like, that may be used for detection of cleaved products in the assay. Among the advantages available with a liquid substrate of the type described herein should be an assay with increased sensitivity to the action of glycosaminoglycan endoglycosidases. This increased sensitivity would at least in part relate to an enhanced availability in solution to soluble enzymes.

The molecular tag at one end of the glycosaminoglycan could be either a small molecule, such as fluorescein or biotin, or a larger molecule, such as a peptide or a protein. The linkage of this molecule to an end of the glycosaminoglycan substrate must not significantly inhibit the hydrolysis of the tagged glycosaminoglycan by the glycosaminoglycan endoglycosidase. The molecular tag should have the ability to act as a potential 'handle' for the labelled glycosaminoglycan chain and for the residue of the glycosaminoglycan chain remaining after cleavage by a glycosaminoglycan endoglycosidase. As a 'handle', the molecule would be able to act as a point of attachment for a protein molecule having affinity for the bound tagging molecule. Such a protein-molecule relationship will enable tagged portions of the labeled glycosaminoglycan to be readily separated from labeled but untagged portions liberated by endoglycosidase-induced hydrolysis of glycosaminoglycan substrate hydrolysis. The molecular tag should be either: (a) a haptenic molecule capable of generating specifically binding antibodies when attached to a carrier such as a protein and immunogenically administered to an animal; (b) a segment of or a whole immunogenic substance such as a protein or peptide; or (c) a substance having a high binding affinity for existent proteinaceous molecules such as avidin or protein A, for example.

Following incubation with samples containing endoglycosidase activity, the uncleaved products may then be separated from the cleaved products by incubation with, for example, solid-phase antibodies having an affinity for the tag. Proteins other than antibodies that bind the molecular tag that has been attached to the end of the glycosaminoglycan may also be used to separate uncleaved glycosaminoglycan. If solid phase antibodies or solid phase binding proteins are used, the solid phase may be any support that can be readily coupled or absorbed to antibodies or binding proteins and that can affect a separation of cleaved product from uncleaved substrate. Commonly-used examples of solid phase include agarose; Sepharose; polymers, such as polystyrene; glass; cellulose and glass beads; and magnetizable beads. The solid-phase could be in the form of large or small particles or a tube or microtiter plate or other device that is readily adaptable to the detection system.

The separation of cleaved from uncleaved glycosaminoglycan products can also be achieved by an immunoprecipitation reaction that does not require antibodies to be linked to a solid phase (see Morgan et al. (1962) Proc. Soc. of Exp. Biol. Med., V 110, pp 29–35). The precipitating antibodies could be directed toward the molecule tagged at the end of the glycosaminoglycan chain.

To facilitate binding at one end to a solid matrix, a further modification of labeled glycosaminoglycan was needed. This modification involved the placement of a primary amino group at one end of the labeled glycosaminoglycan. A preferable method of accomplishing this placement was to incubate the labeled glycosaminoglycan with an ammonium salt and sodium cyanoborohydride at an alkaline pH. A Schiff base initially forms between ammonia and the aldehydic carbonyl group of the terminal hexose. This Schiff base is reduced to a primary amine by the sodium cyanoborohydride.

The synthetic steps to produce the solid phase substrate of the present invention generally include partial N-deacylating, for example, by hydrazinolysis, or N-desulfating, for example by solvolysis in dimethylsulfoxide; an N-acylating step with labeled acyl anhydride or halide for radioisotopic labeling; a reductive amination step; and coupling to a solid matrix through the newly introduced terminal amine. An often preferred final step, to insure that no amine-reactive functions remain on the solid matrix, is to incubate the product of the matrix-labeled amine-terminal glycosaminoglycan coupling with sodium cyanoborohydride and a compound bearing a free amino group. This latter compound may, for example, be one such as ethanolamine or glycine ethyl ester.

The substrates and procedures of the present invention present numerous advantages for the assay of glycosaminoglycan endoglycosidase enzymic activity. For example, the substrate of the present invention is bound to a solid matrix via a single carbohydrate-bound amino ligand and yields a linear pattern of enzymatic products.

In the past, proteoglycans containing glycosaminoglycans as well as a bound protein component have been bound to a solid matrix of cyanogen bromide-activated agarose. The proteoglycan was thereby likely bound to the agarose primarily through its proteinaceous component. Thus, both proteolytic as well as glycosaminoglycan endoglycosidic activity may liberate a soluble product. The specificity of the assay for enzymic activity of the endoglycosidases is less than the results shown with the present invention.

A heparanase (heparan sulfate endoglycosidase) obtained from a human melanoma cell line was found to only partially degrade N-desulfated, N-acetylated heparin. This same enzyme preparation was found to efficiently cleave N-desulfated heparan sulfate as well as N-desulfated N-acetylated heparan sulfate into characteristic degradation fragments.

While there are many glycosaminoglycan endoglycosidases, heparan sulfate endoglycosidase or heparanase, the endoglycosidase utilizing heparan sulfate as a preferred substrate, was chosen as a typical example to demonstrate a preferred embodiment of the present invention. Additionally, an N-hydroxy succinide agarose derivative was selected as a preferred solid matrix to couple labeled amine-terminal heparan sulfate to produce a solid phase substrate. Heparanase activity produced soluble radioisotopically labeled products as demonstrated specifically in many of the following examples.

Figure 8:
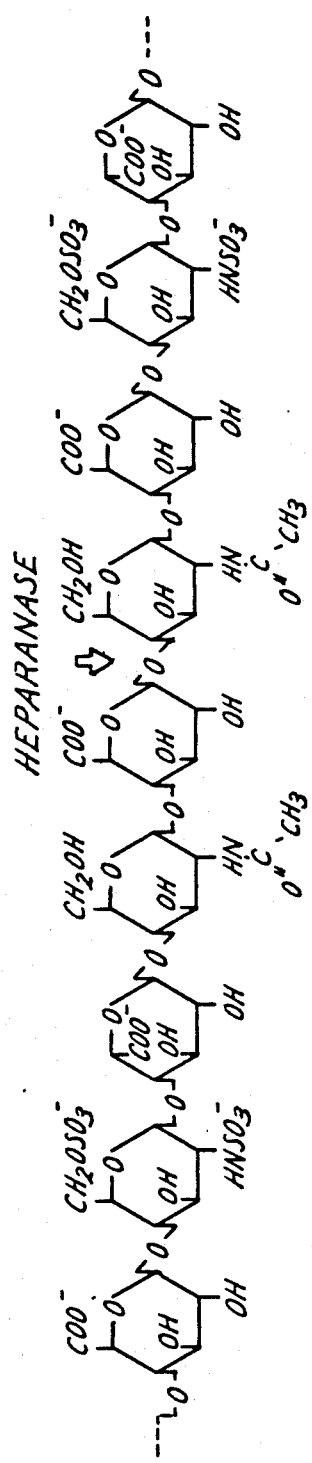
FIG. 8 shows the position of substrate hydrolysis for melanoma heparanase.
Figure 8:
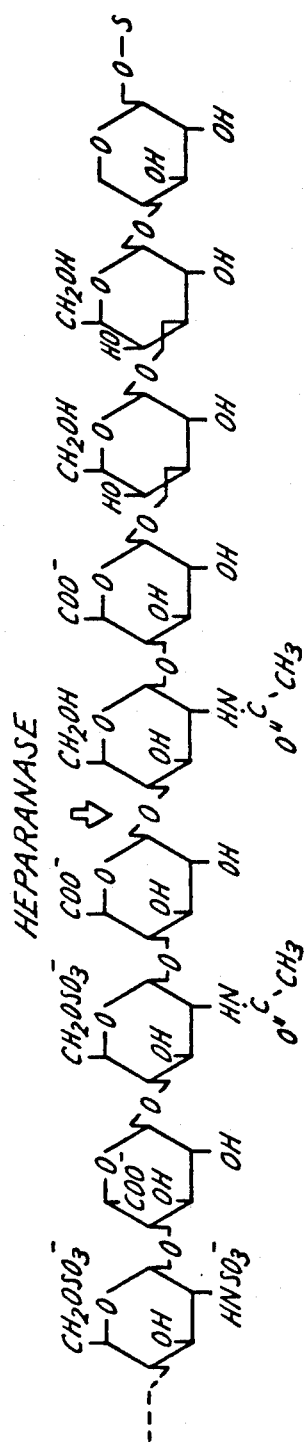

Melanoma heparanase is an endo-beta-glucuronidase which specifically cleaves HS at intrachain sites. Such melanoma heparanase specificity is illustrated in FIG. 8. Thus, the separation of the reaction products from the substrates based on their size is required for the heparanase assay. Although previously established methods such as polyacrylamide gel electrophoresis and high-speed gel permeation chromatography are useful for the characterization of degradation fragments, they are not suitable for rapid and microscale quantitative assays of large sample numbers. To perform rapid quantitative assays, a covalently linked substrate is required. The presently developed solid phase assay substrate is partially N-deacetylated or N-desulfated, N-[$^3$H or $^{14}$C]-acetylated HS coupled with Affi-Gel 15. In this substrate a HS derivative is linked to agarose through only one covalent bond (FIG. 1). This product is one of the most sensitive endoglycosidase substrates to be developed. This substrate has now been successfully used for mouse and human melanoma heparanase assays. The same type of derivative has also been produced by using Reacti-Gel (NW-65F) (Pierce, Rockford, IL). However, both Affi-Gel 15 and Reacti-Gel (HW-65F) use quite large particles and these retain significant amounts of high molecular weight materials in the gel matrices. This may be a problem in some quantitative heparanase assays, therefore, we developed a more desirable assay substrate by using Affi-Gel 701 or 702 (Bio-Rad) which are approximately 1–3 microns in diameter with an exclusion limit of $M_r$ 10,000. The specific synthetic procedure was as follows. Radiolabeled HS was reduced with sodium borohydride to form a sugar alcohol at the reducing terminal. The sugar alcohol was converted to a primary aldehyde by periodate oxidization. This aldehyde group was then linked to amino-derivatized beads, such as Affi-Gel 701, through a Schiff base and stabilized by reduction with sodium cyanoborohydride. Yet further proposed procedures, simliar to our previously developed methods, are contemplated as useful. Radiolabeled HS whose amino groups have been sulfated or acetylated should be aminated at the reducing terminal with ammonia under reducing conditions. Affi-Gel 702 should be converted to an amino-reactive bead by derivatization with N-hydroxysuccinimide or N,N'-carbonyldiimidazole, and then the aminated radioactive HS should be linked to amino-reactive Affi-Gel 702. The substrate may be made more radioactive by use of $^{125}$I-labeled HS, although iodination of HS with Bolton and Hunter Reagent may be disadvantageous because of potential structural change. On the other hand, the assay may also be improved by use of fluorescein-labeled HS for routine clinical studies, and fluorescein-labeled HS is suitable for a rapid analysis of degradation fragments on HPLC equipped with a flow fluorescence detector.

The assay measuring levels of a glycosaminoglycan endoglycosidase such as heparan sulfate endoglycosidase (heparanase) may also be performed in an immunoassay format using polyclonal and/or monoclonal antibodies raised to the endoglycosidase. Preferably, antibodies with relatively low cross-reactivity to other endoglycosidases, such as the platelet endoglycosidase described by Oldberg, et al. (1980) *Biochem.*, V 19, pp 5755–5762, can be used. The antibodies may be used with a variety of immunoassay techniques to measure the endoglycosidase protein directly. The endoglycosidase may be measured by either a radioimmunoassay described by Berson and Yalow (1968) *Clin. Chem, Acta.*, V 22, p 51 or an immunoradiometric (IRMA) assay described by Miles, et al. (1976) *Anal. Biochem.*, V 61, pp 209–224 using 125I-labeled antigen or antibody. The endoglycosidase may also be measured by an enzyme immunoassay that uses either a competitive-binding assay or a "sandwich" assay analogous to an IRMA and using alkaline phosphatase, horse radish peroxidase, or any other enzyme coupled to an antibody or to the endoglycosidase as reviewed by Wisdom (1976) *Clin. Chem*, V 22, pp 1243–1255.

The endoglycosidase may also be measured in these assays by using fluorescein or other flourescent compounds as reviewed by Gerson (1984) *J. Clin. Immunoassay*, V 7, pp 73–81, by chemiluminescence as reviewed by Weeks and Woodhead (1984), *J. Clin Immunoassay*, V 7, pp 82–89, or by other labels. In all of these assays, the bound endoglycosidase may be separated from the unbound endoglycosidase by a variety of techniques. These include solid-phase immobilization of a primary (anti-endoglycosidase) antibody, avidin-biotin separation using a biotin-labeled antibody and solid phase avidin, "double antibody" precipitation, or by using solid phase antibody against a hapten like fluorescein coupled to a primary antibody, or by using a solid phase "second antibody". ("Double antibody" is defined as a heterologous antibody that binds the anti-endoglycosidase antibody as in Midley, et al. (1969) *Acta Endocrinol.*, V 63, Supp. 142, p 247).

The solid phase systems mentioned above can include polymers, such as polystyrene; agarose; sepharose; cellulose; glass beads; and magnetizable particles of cellulose or other polymers. The solid-phase can be in the form of large or small beads or particles; tubes; plates; or other forms.

Kits useful in the present invention include those of the general type described by Szczesniak, U.S. Pat. No. 3,899,298. Such kits comprise a carrier being compartmentalized to receive at least one, or at least two or ot least three or more containers and to maintain said containers in closed confinement. A first container may contain purified anti glycosaminoglycan endoglycosidase antibody (preferably monoclonal), either in solution, in freeze-dried form or covalently bound to the inside thereof, such as for example if such container is a test tube. A second container may then contain a second anti glycosaminoglycan endoglycosidase antibody (also preferably monoclonal). Alternatively, another container may contain detectably labeled glycosaminoglycan endoglycosidase antigen. At the time of testing for glycosaminoglycan endoglycosidase antigen in the sample, the sample is added to the first container containing the monoclonal antibody, incubated, and then antibody from the second container is added thereto to provide a "sandwich". The antibody in the second container may be detectably labeled as, for example, by a radiolabel or an enzyme label. Another container in the kit may contain appropriate enzyme substrate in order to carry out the "ELISA" methodology. Any number of variations or permutations consistent with the various techniques for use in the detection of glycosaminoglycan endoglycosidase antigen may be envisioned for the preparation of a kit. These are all matters of choice, determined by the ease of handling, rapidity and efficiency of the testing.

Quantitative analysis of glycosaminoglycan endoglycosidase antigen can be carried out by interpolation into a standard curve, as is known in the art. A multiplicity of container means, each one having a different amount of glycosaminoglycan endoglycosidase antigen can be present in the kit for such a purpose.

In still another embodiment, the antibody can be immobilized onto plastic strips which are then brought into contact with the samples suspected of containing glycosaminoglycan endoglycosidase antigen. Subsequently, the strip is contacted with a solution containing a second, enzyme labeled anti glycosaminoglycan endoglycosidase antibody; this results in a sandwich forming on the strip. Finally, introduction of the strip into a color developing solution (such as substrate for the enzyme) and detection of color, is a rapid efficient and inexpensive method for qualitatively, and even roughly quantitatively determining glycosaminoglycan endoglycosidase antigen in animal samples.

The immunoassays of the present invention may use antibodies which are very discriminating between the different glycosaminoglycan endoglycosidases, particularly for heparan sulfate endoglycosidase. The methodology described herein should be superior in sensitivity and ease to other known methods of glycosaminoglycan endoglycosidase detection.

In an analogous manner, kits are easily constructed comprising labeled glycosaminoglycan affixed, preferably through its amino-terminal end to a molecular tag as described above. Such a kit would also comprise a specific binding agent capable of removing tagged glycosaminoglycan or tagged fragments thereof from solution. The specific binding agent may already be bound to a solid matrix or may be so bound by the user of the kit and assay. Preferred binding agents are proteins, more preferably, antibodies and most preferably, monoclonal antibodies.

The development of specific diagnostic tests for infections of glycosaminoglycan endoglycosidase has become medically desirable for purposes such as detection of tumors. Such specific diagnostic tests as described herein may be developed through the use of monoclonal or polyclonal antibodies specifically binding to glycosaminoglycan endoglycosidase.

These examples are presented to describe preferred embodiments and utilities of the present invention and are not meant to limit the present invention unless otherwise specified in the claims appended hereto.

MATERIALS AND METHODS

Glycans and enzymes. Bovine lung heparan sulfate was (HS) a kind gift from Dr. N. Di Ferrante (Baylor College of Medicine, Houston, Tex.) and its average $M_r$ was determined as 34,000 by sedimentation equilibrium (Nakajima, M., et al., (1984) J. Biol. Chem. V 259, pp 2283-2290 and Irimura, T., et al., (1983) Anal. Biochem. V 130, pp 461-468). Heparin ($M_r$ 11,000) from porcine mucosal tissue was kindly donated by Drs. M. B. Mathews, J. A. Cifonelli, and L. Roden (University of Chicago, Ill.). Chondroitin 6-sulfate (C6S) from shark cartilage was obtained from Miles Scientific (Naperville, Ill.) and further purified by gel chromatography; its average $M_r$ was determined as 60,000 as described previously (Irimura, T., et al., (1983) Anal. Biochem. V 130, pp 461-468). Heparin from bovine lung and porcine intestinal mucosa and N-acetyl-D-glucosamine were obtained from Sigma Chemical Co. (St. Louis, Mo.). Monosialosyl biantennary complex-type glycopeptide UB-I-b ($M_r$ 2190) was prepared from thyroglobulin (Sigma) (Irimura, T., et al., (1983) Anal. Biochem. V 130, pp 461-468). Heparitinase from *Flavobacterium heparinum* (EC4.2.2.8) was obtained from Miles Scientific.

High-speed gel permeation chromatography. High-speed gel permeation chromatography was carried out using a high pressure liquid chromatograph system (LDC, Riviera Beach, Fla.) equipped with two sequential columns (0.7×75 cm) of Fractogel (Toyopearl) TSK HW-55(S) (MCB, Gibbstown, N.J.) as described previously (Irimura, T., et al., (1983) Anal. Biochem. V 130, pp 461-468). A one hundred microliter aliquot of sample solution was delivered into the injection port, and the chromatographic elution was performed with 0.2M sodium chloride at a flow rate of 1.0 ml/min at 55° C. (Irimura, T., et al., (1983) Anal. Biochem. V 130, pp 461-468). In the analysis of radiolabeled materials, fractions corresponding to each 36 s of elution (0.6 ml) were collected and mixed with 3.0 ml of Liquiscint (National Diagnostics, Comerville, N.J.), and counted on a Beckman LS 2800 liquid scintillation counter (Beckman Instruments, Irvine, Calif.).

Cellulose acetate electrophoresis. Glycosaminoglycans were analyzed by cellulose acetate electrophoresis according to the method of Cappelletti et al. (Cappelletti, et al., Anal. Biochem., V 99, pp 311-315).

Titan III Zip Zone cellulose acetate plates (6.0×7.6 cm, Helena Laboratories, Beaumont, Tex.) were used, and electrophoresis was carried out at 70 V for 60 min in 0.5 M pyridine-acetate (pH 5.0), instead of 0.1M barium acetate buffer employed by Cappelletti et al. (Cappelletti, et al., Anal. Biochem., V 99, pp 311-315). During the electrophoresis the buffer and cellulose acetate plates were kept below 4° C. using petroleum ether cooled with ice.

N-Desulfation and acetylation of HS. N-desulfation of HS was conducted by the methods of Nagasawa and Inoue (Nagasawa et al., (1977) Methods in Carbohyd. Chem. V 8, pp 291-294). The sodium salt of purified HS was converted to the pyridinium salt by cation exchange chromatography on a column of AG50WX8(H+ form, Bio-Rad, Richmond, Calif.) and neutralization with pyridine. Complete N-desulfation and partial N-desulfation of HS was carried out by solvolysis of the pyridinium salt of HS in 95% dimethylsulfoxide (DMSO) and 5% water for 120 min at 50° C., and for 60 min at 20° C., respectively. The pH of the reaction mixture was adjusted to 9.0 by the addition of 0.1M sodium hydroxide; and then the mixture was dialyzed against running tap water overnight and then against distilled water for 20 h. The N-acetylation of N-desulfated HS was performed in 4M sodium acetate, pH 8.0, containing 4% acetic anhydride, 15% methanol for 3 h at 4° C. The reaction mixture was dialyzed against running tap water overnight and then against distilled water, and the mixture was then lyophilized.

Radioisotope labeling of HS. To study the effects of chemical modification of HS on its susceptibility to melanoma heparanase, HS was labeled with tritium at the reducing end as described previously (Nakajima, M., et al., (1984) J. Biol. Chem. V 259, pp 2283-2290). One milligram of purified HS was reduced with 2 mCi of NaB[$^3$H]$_4$(340 mCi/mmol; New England Nuclear, Boston, Mass.) in 0.1M sodium borate buffer, pH 8.0, for 5 h at 25° C. After acidification to pH 5 with acetic acid, the reaction mixture was chromatographed on a column (1.0×105 cm) of Sephacryl S-200 equilibrated with 0.2M pyridine-acetate buffer, pH 5.0. Fractions of $^3$H-labeled HS with specific $M_r$ were collectd and lyophilized. To synthesize radiolabeled HS for a solid-phase heparanase substrate, partially N-desulfated HS was N-acetylated with [1-$^{14}$C]acetic anhydride. Fifteen milligrams of partially N-desulfated HS were incubated with 0.15 mCi of [1-$^{14}$C]acetic anhydride (10.0 mCi/mmol; New England Nuclear) in 4M sodium acetate, pH 8.0, for 4 h at 4° C.; and then further incubated with 4% acetic anhydride in the same buffer for 4 h at 4° C. The reaction mixture was extensively dialyzed against distilled water, and then lyophilized. High $M_r$ fractions of partially N-desulfated N-[$^{14}$C]acetylated HS (PNDS-N[$^{14}$C]Ac-HS) were obtained by gel chromatography on a column of Sephacryl S-200 as described above.

Reductive Amination and Coupling of $^{14}$C-labeled HS to amino-reactive agarose beads. The reducing terminal saccharides of $^{14}$C-labeled HS were reductively aminated as follows. PNDS-N[$^{14}$X]Ac-HS (5 mg) was dissolved in 5 ml of distilled water and mixed with 5 ml of 4M ammonium formate and 0.8M sodium cyanoborohydride in methanol, and then incubated at 50° C. for 7 days. The reaction mixture was dialyzed against distilled water and lyophilized. The reductively aminated products were dissolved in 10 ml of 0.1N sodium bicarbonate, pH 8.5, and mixed with Affi-Gel 15 (or Affi-Gel 10; Bio-Rad) prepared from the original suspension by successive washing in 2-propanol and then ice-cold distilled water. The mixture was incubated at 4° C. for 24 h with gentle mixing. The pH was then adjusted to pH 8.5 with 0.1N sodium bicarbonate and the incubation further contined. After 24 h the unreacted sites on the Affi-Gel 15 were blocked by addition of 1 ml of 1M glycine ethyl ester (pH 8.0), and the beads were again incubated for 6 h at 4° C. After the reaction was complete, the coupling products were extensively washed in 1.5M sodium chloride, and incubated in 0.1M sodium acetate, 0.15M sodium chloride, 0.2% Triton X-100, and 0.05% sodium azide (pH 6.0) at 37° C. overnight. The products were further washed in the same buffer and stored at 4° C.

The summary of the above described synthetic procedures is shown in FIG. 1.

Chemical deacetylation and radioactive reacetylation of heparan sulfate and its coupling to agarose beads. $^{14}$C- or $^3$H-labeled HS were prepared by chemical deacetylation and radioactive reacetylation as follows. Nine milligrams of bovine lung HS (provided by Dr. N.

Di Ferrante, Baylor College of Medicine, Houston, Tex.) were dried with 1 mg hydrazine sulfate over phosphorous pentoxide under vacuum at 50° C. for 48 hrs. Anhydrous hydrazine (0.5 mg, Pierce Chemical, Rockford, Ill.) was added to the dried HS, and the mixture was heated in a tightly screwed tube under nitrogen atmosphere at 100° C. for 1 hr. After the reaction, the hydrazine was removed by repeated evaporation with toluene over sulfuric acid dessicant under vacuum conditions. To separate deacetylated HS from residual reagents and partial degradation products, completely dried residue was dissolved in 0.5 ml water and subjected to gel filtration on a 0.8×30 cm column of Bio-Gel p-10 (400 mesh) eluting with distilled water. The void volume fraction was collected and lyophilized. The yield was approximately 60% by weight. The N-deacetylated HS was then N-acetylated with 50 uCi [$^{14}$C]-acetic anhydride (10 mCi/mmole: NEN, Boston, Mass.) or 5 mCi 3H-acetic anhydride (400 mCi/mmole:NEN) in 0.5 ml of 4M sodium acetate for 18 hrs. Complete N-Acetylation was accomplished by mixing with 0.1 ml of non-labeled acetic anhydride for 1 hr. $^{14}$C- or $^{3}$H-labeled HS was purified on the same BioGel P-10 column as described above.

For the solid-phase heparanase assay, $^{3}$H-HS was aminated at the reducing terminal with 2M ammonium acetate in the presence of 0.4M sodium cyanoborohydride in 50% methanol at 50° C. for 6 days. Aminated $^{3}$H-HS was purified by gel filtration as above, and the resulting solution was made to 0.1M in sodium carbonate. To $10^6$ cpm of aminated $^{3}$H-HS, 1.0 ml Affi-Gel 15 was added after the gel beads were washed with isopropanol and chilled water according to the manufacturer's recommendations. The coupling reaction was continued at 4° C. for 48 hrs with continous agitation. The agarose beads were then washed with 4M sodium chloride repeatedly to remove noncovalently attached $^{3}$H-HS from the beads.

Melanoma cells and cell culture. The high lungcolonizing metastatic murine B16 melanoma subline (B16-F10) and fourteen established cell lines of human malignant melanoma were employed in this study. The human melanoma cell lines used were: SK-MEL-19, SK-MEL-23, SK-MEL-93(DX1), SK-MEL-93(DX3), SK-MEL-93(DX6), Hs294T, Hs852T, HS939, T294,M40, RON, BMCL, A375 parent, and A375 Met Mix. A375Met Mix cells were prepared from spontaneous lung metastases of A375 parental cells in the athymic nude mice and both A375 cell lines were provided by Dr. I. J. Fidler (The University of Texas-M.D. Anderson Hospital and Tumor Institute, Houston, Tex.). Melanoma cells were grown on plastic tissue culture dishes in a 1:1 mixture of Dulbecco's modified minimum essential medium and Ham's F12 medium (DMEM/F12; Gibco Laboratories, Grand Island, N.Y.) with 10% fetal bovine serum (Hyclone, Sterile Systems, Inc., Logan, Utah) and without antibiotics, under humidified conditions in a 95% air-5% $CO_2$ atmosphere. All cell cultures were determined to be free of mycoplasma contamination with the use of mycoplasma detection system (BRL MycoTest; Bethesda Research Laboratories, Gaithersburg, M).

Preparation of cell extracts. Subconfluent melanoma cells were harvested by treatment for 10 min with 2 mM ethylene diamine tetracetic acid (EDTA) in $Ca^{2+}$, $Mg^{2+}$-free DPBS. Single cell suspensions were washed twice by brief centrifugation in 0.14M sodium chloride, 10 mM Tris-HCl buffer, pH 7.5, and checked for viability (usually >95%) by trypan blue dye exclusion. Cells were suspended in chilled 50 mM Tris-HCl buffer, pH 7.5, containing 0.5% Triton X-100 at a concentration of $6\times10^6$ cells/ml and extracted for 5 ml at 25° C. and for an additional 1 h at 4° C. The supernatant was collected after centrifugation at 9800×g for 5 min at 4° C. Protein contents in the centrifuged extracts were determined by a modification of the Lowry technique to correct for the presence of Triton X-100 in the samples (Nakajima, M., et al., (1984) J. Biol. Chem. V 259, pp 2283–2290).

Enzymatic degradation of unmodified and modified HS. In the enzymatic degradation experiments the $^{3}$H-labeled HS substrate (10 ug) was incubated with a B16-F10 cell extract (80 ug protein) in 200 ul of 0.1M sodium acetate buffer (pH 6.0) containing 0.15M sodium chloride, 0.2% Triton X-100 and 0.05% sodium azide (reaction buffer A) in the presence of 20 mM D-saccharic acid 1,4-lactone (SAL, a potent exo-beta-glucuronidase inhibitor). The incubation was carried out at 37° C. with gentle mixing, and was terminated by chilling the mixture to 4° C. and adding 20 ul of trichloroacetic acid to a final concentration of 5%. The supernatant was obtained by centrifugation at 9800×g for 5 min and it was subjected to analysis by high-speed gel permeation chromatography.

Heparanase assay using a solid-phase substrate. A suspension of PNDS-N[$^{14}$C]Ac-HS coupled to Affi-Gel 15 was mixed with a melanoma cell extract and incubated in 400 ul of reaction buffer A containing 20 mM SAL. The enzyme reaction was terminated by chilling the solution to 4° C. and mixing it with 40 ul of 50% trichloroacetic acid. After incubation for 10 min at 4° C., the mixture was centrifuged at 9800×g for 5 min, and the supernatant was withdrawn. Two hundred microliter aliquots of the supernatant were mixed with 55 ul of 1.0N sodium hydroxide and 4 ml of Liquiscint (National Diagnostic) and counted in a Beckman LS 2800 liquid scintillation counter.

Effects of N-desulfation and N-acetylation of HS on HS degradation by melanoma heparanase. To label purified HS with radioactive molecules without use of linking reagents that might cause significant changes in HS molecular structure, we replaced some of the N-sulfate groups with N-[$^{14}$C]acetyl groups. This idea was based on our previous observation that B16 melanoma heparanase was highly active against various HS molecules but inactive against heparin, and that HS differs from heparin in its high N-acetyl and low N-sulfate contents.

Figure 2:
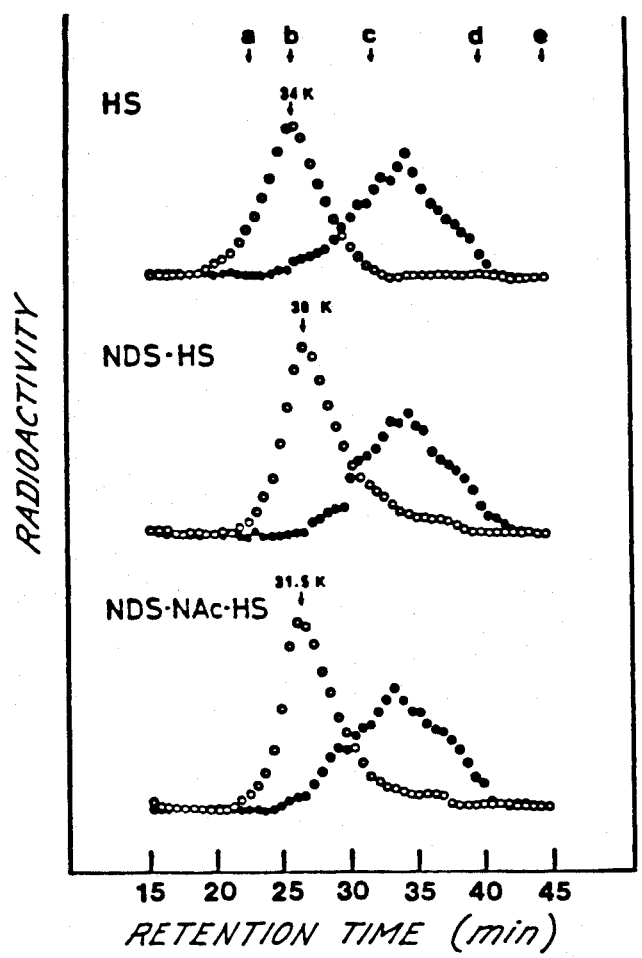
FIG. 2. Elution profiles on high-speed gel permeation chromatography of unmodified- and chemically modified-HS before and after treatment with B16 melanoma heparanase. HS, heparan sulfate; NDS-HS, N-desulfated heparan sulfate NDS-HAc-HS, N-desulfated N-acetylated heparan sulfate. These glycans labeled with tritium at the reducing termini (o) and their fragements produced by the incubation with B16 melanoma-cell extracts in the presence of SAL (o), were chromatographed on two sequential 0.7×75-cm columns of Fractogel-TSK HW-55(S) with 0.2M sodium chloride at a flow rate of 1.0 ml/min at 55° C. Arrows (a)-(e) indicate the elution positions of the standard glycans: (a) C6S from shark cartilage ($M_r$ 60,000); (b) HS from bovine lung ($M_r$ 34,000); (c) heparin from porcine mucosal tissue ($M_r$ 11,000 ; (d) monosialosyl biantennary complex-type glycopeptide from porcine thyroglobulin ($M_r$ 2190); (e) N-acetyl-D-glucosamine ($M_r$ 221).

The effect of N-desulfation and N-acetylation of HS on its susceptibility to melanoma heparanase was assessed using HS labeled with tritium at the reducing terminal saccharide. Since HS purified from bovine lung had mostly N-acetyl-D-glucosamine at the reducing ends (Nakajima, M., et al., (1984) J. Biol. Chem. V 259, pp 2283–2290), HS was reduced with NaB[$^{3}$H]$_4$. HS labeled with tritium at the reducing end was N-desulfated by solvolysis with DMSO, and N-desulfated [$^{3}$H]HS was then N-acetylated with acetic anhydride. These three $^{3}$H-labeled, chemically modified HS molecules were analyzed by cellulose acetate electrophoresis in 0.5M pyridine-acetate buffer, pH 5.0. The relative mobilities of HS N-desulfated HS (NDS-HS) and N-desulfated N-acetylated HS (NDS-NAc-HS) under the electrophoresis conditions described in the materials and methods were 3.30, 2.55, and 2.90, respectively. These findings indicated that N-desulfation of HS resulted in a significant loss of negative charge; however, the total negative charge was partially recovered by acetylation of free amino groups. The average molecular size of NDS-HS and NDS-NAc-HS were determined by high-speed gel permeation chromatography, and were found to be 30,000 and 31,500, respectively (FIG. 2). Each of HS, NDS-HS and NDS and NDS-NAc-HS was incubated with B16 melanoma cell extracts in the presence of SAL (a potent exo-beta-glucuronidase inhibitor), and the incubation products were analyzed by high-speed gel permeation chromatography. All these substrates were cleaved by melanoma heparanase at high rates and the elution profiles of their degradation produts were similar, although the $M_r$ of the fragments produced were characteristic for each substrate (FIG. 2). Degradation of each of the chemically modified HS was totally inhibited by addition of amounts of heparin purified from bovine lung or porcine intestinal mucosa (data not shown). The results indicated that N-sulfate in HS may not be important for its recognition and cleavage by melanoma heparanase, and that the chemical modification of sulfated amino groups in HS does not significantly affect its degradation by heparanase.

N-Desulfated and N-acetylated heparin. The known structures of HS and heparin suggested that N-desulfation and subsequent N-acetylation of heparin may generate local structures similar to those present in HS. Heparin is a potent inhibitor of B16 melanoma heparanase (Nakajima, M., et al., (1984) J. Biol. Chem. V 259, pp 2283-2290); however, its heparanase inhibitory activity is lost by the removal of N-sulfate (Irimura, et al. (1985) J. Cell. Biochem. V 9A, p 148). Since the results above suggested that N-sulfate in HS is unnecessary for its cleavage by melanoma heparanase, N-desulfated N-acetylated heparin was used as a heparanase substrate. Heparin from porcine intestinal mucosa ($M_r$ 11,000) previously labeled with tritium at its reducing end (Nakajima, M., et al., (1984) J. Biol. Chem. V 259, pp 2283-2290) was N-desulfated and then N-acetylated by the procedures employed in the preparation of NDS-NAc-HS. The product, N-desulfated N-acetylated heparin (NDS-NAc-heparin), had an apparent $M_r$ of about 10,500 as determined by high-speed gel permeation chromatography; and its relative electrophoretic mobility on cellulose acetate in 0.2M pyridine-acetate buffer, pH 5.0, was 0.87 when the electrophoretic mobility of $^3H$-labeled heparin was taken as 1.00. $^3H$-labeled heparin and $^3H$-labeled NDS-NAc-heparin were incubated with B16 cell extracts and the reaction products were analyzed by highspeed gel permeation chromatography. Percentage degradation of the original substrates was calculated from the decrease in area of the high $M_r$ half of the substrate peak as reported previously (Nakajia, M., et al., (1984) J. Biol. Chem. V 259, pp 2283-2290). During the first 6 h incubation with a B16 cell extract, less than 5% of heparin was degraded, while approximately 20% of the NDS-NAc-heparin was fragmented. However, NDS-NAc-heparin was not further cleaved and the major peak of NDS-NAc-heparin on high-speed gel permeation chromatography did not shift to a lower $M_r$ even after a prolonged incubation. This suggested that N-desulfation and subsequent N-acetylation of heparin can result in the generation and/or exposure of heparanase-susceptible glucuronosyl linkages in a part of the heparin molecule. Thus, NDS-NAc-heparin cannot be utilized as a melanoma heparanase assay substrate.

Synthesis of solid-phase substrate for melanoma heparanase assay. The procedure for the synthesis of a solid-phase substrate for heparanase is illustrated in FIG. 1. To minimize the radiolabeling effects on the HS structure, HS was only partially N-desulfated by solvolysis in 95% DMSO and 5% $H_2O$ for 1 h at 20° C. Partially N-desulfated HS was acetylated with [1-$^{14}$C]acetic anhydride as described in the material and methods section. The remaining free amino groups were completely acetylated with acetic anhydride. These steps yielded PNDS-N[$^{14}$C]Ac-HS, ($M^r$ 33,000) with radioactivity of 294 cpm/ug. The relative mobility of PNDS-N[$^{14}$C]Ac-HS on cellulose acetate electrophoresis was 3.15, indicating that the total negative charge of PNDS-N[$^{14}$C]Ac-HS is much closer to that of unmodified HS than is that of NDS-NAc-HS as expected.

The reducing terminal saccharides of PNDS-N[$^{14}$C]Ac-HS were reductively aminated with 2M ammonium formate and 0.4M sodium cyanoborohydride in 50% methanol. The products having free amino groups only on the reducing termini were then coupled to aminoreactive agarose beads such as Affi-Gel 10 or Affi-Gel 15. Incubation of 5 mg of PNDS-N[$^{14}$C]Ac-HS with 0.5 ml of packed Affil-Gel 15 resulted in the immobilization of 10.2% PNDS-N[$^{14}$C]Ac-HS onto Affi-Gel 15 (0.51 mg PNDS-N[$^{14}$C]Ac-HS per 0.5 ml of gel). Increasing concentrations of PNDS-N[$^{14}$C]Ac-HS up to 10 mg per 0.5 ml of Affi-Gel 15 did not significantly affect the coupling efficiency under the conditions used.

PNDS-N[$^{14}$C]Ac-HS was also conjugated to Affi-Gel 10 under the same conditions used for the coupling of PNDS-N[$^{14}$C]Ac-HS to Affi-Gel 15. However, the coupling efficiency was low, less than 1%, between pH 7.5 and 8.5. Therefore, a positive charge spacer at the aminoreactive site of Affi-Gel 15 may be important in the effective coupling of PNDS-N[$^{14}$C]Ac-HS to Affi-Gels. Using Affi-Gel 15, one of the best heparanase assay substrates was produced: PNDS-N[$^{14}$C]Ac-HS immobilized on agarose through only one covalent linkage at the reducing terminal end.

Figure 3:
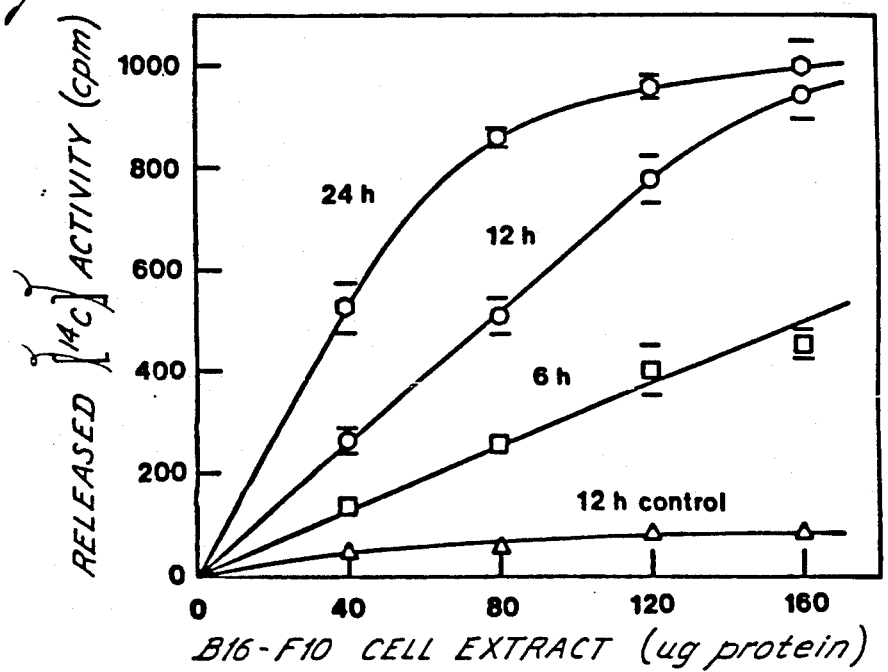
FIG. 3. Dose dependent degradation of partially N-desulfated N[$^{14}$C]acetylated heparan sulfate PNDS-N[$^{14}$C]Ac-HS) immobilized on agarose ty B16 melanoma cell heparanase. The PNDS-N[$^{14}$C]Ac-HS (4500 cpm) immobilized on agarose was incubated with various amount of B16 cell extract for 6 h (□), 12 h (o), and 24 h (◇) , or with various amounts of heat inactivated (100° C., 5 min) B16 cell extract for 12 hr (Δ) in the presence of SAL. The released radioactivity in a half volume of the supernatant versus the amount of cell extract added (ug protein) was plotted.

Enzymatic degradation of PNDS-N[$^{14}$C]Ac-HS immobilized on agarose gel beads. The susceptibility of PNDS-N[$^{14}$C]Ac-HS immobilized on agarose gel to HS degrading enzymes was examined by incubating the substrates (4500 cpm, 15 ug) with bacterial heparitinase (EC.4.2.2.8) at a concentration of 5 units/ml in 0.1M sodium acetate buffer, pH 7.0, containing 1 mM calcium acetate (Linker, et al. (1972) Methods Enzymol. V 28, pp 902-911). Most of $^{14}$C activity (82%) appeared in the supernatant of the incubation mixture after a 24 h incubation, indicating that PNDS-N[$^{14}$C]Ac-HS immobilized on agarose is very susceptible to HS degrading enzymes. The remainder of the PNDS-N[$^{14}$C]Ac-HS was not released from the gel, even after prolonged incubation. This could be explained by the limitation of using a Flavobacterium heparitinase. The same amount of substrate (4500 cpm) was incubated with B16 cell extract for various periods in the presence of 20 mM SAL to prevent the sequential degradation by exogylcosidases. The relationships between the amounts of cell extract (ug protein) added and the release $^{14}$C activity are shown in FIG. 3. In this case, the maximum amount of released $^{14}$C activity were 56% of the total $^{14}$C activity present in the solid-phase substrates. A portion of the $^{14}$C activity could not be released by melanoma heparanase, since the incubation of HS or of chemically modified HS with a B16 cell extract resulted in the production of large fragments with the original reducing termini (FIG. 2). A linear relationship between the amount of cell extract added and the release $^{14}C$ activity was found for each incubation period (FIG. 3). Since the results from the 12 h incubation were linear over the widest range of cell extract amounts, we measured the degradation of PNDS-n[$^{14}$C]Ac-HS during a 12 h incubation.

The effect of heparin on the degradation of the solid-phase substrates was investigated by addition of substrate-equal amount (15 ug) of heparin from porcine intestinal mucosa or heparin from bovine lung to the incubation mixture containing B16-F10 cell extract (80 ug protein) and PNDS-N[$^{14}$C]Ac-HS immobilized on agarose. The addition of either heparin caused up to 80% inhibition of the degradation of the solid-phase substrates, consistent with our previous results (Nakajima, M., et al., (1984) J. Biol. Chem. V 259, pp 2283–2290).

Measurement of heparanase activity in human melanoma cells by use of PNDS-N[$^{14}$C]Ac-HS immobilizd on agarose beads. Using PNDS-N[$^{14}$C]Ac-H immobilized on agarose beads, the following fifteen human melanoma cell lines were tested for heparanase activity: SK-MEL-19, SK-MEL-23, SK-MEL-93(DX1), SK-MEL-93(DX3), SK-MEL-93(DX6), Hs294T, Hs852T, Hs939, T294, M40, RON, BMCL, A375 parent, A375-Met Mix, and A375M6. All the human melanoma cells showed the ability to degrade HS in the presence of SAL as shown in Table 1. Six of these human malignant melanoma cell lines such as SK-MEL-93(DX1), SK-MEL-93(DX6), Hs939, M40, A375Met Mix, and A375M6 demonstrated significantly greater ability to degrade HS than did mouse B16 melanoma subline F10.

Interestingly, A375Met Mix and A375M6 cells were selected from A375 parental cells by their ability to colonize the lung in athymic nude mice. They were reported to have a high metastatic potential, while A375 parental cells had a very low metastatic potential (Kozlowski, et al. (1984) J. Natl. Cancer Inst. V 72, pp 913–917). Therefore, the heparanase activity of A375 cells may correlate with their spontaneous lung metastatic potential.

We have previously found that intact B16 melanoma cells or B16 cell extracts from sublines of high lung colonization potential degrade purified HS at higher rates than B16 cells of poor lung colonization potential (Nakajima, et al. (1983) Science V 220, pp 611–613), and that B16 melanoma HS degrading endoglycosidase is an endo-beta-glucuronidase (heparanase) (Nakajima, M., et al., (1984) J. Biol. Chem. V 259, pp 2283–2290).

TABLE 1
HEPARAN SULFATE DEGRADATION ACTIVITY IN HUMAN MALIGNANT MELANOMA CELLS

| Melanoma cell lines | Heparan sulfate degradation activity[a] mean ± S.D (cpm) |
|---|---|
| SK-MEL-19 | 379 ± 40 |
| SK-MEL-23 | 397 ± 29 |
| SK-MEL-93(DX1) | 625 ± 36 |
| SK-MEL-93(DX3) | 381 ± 25 |
| SK-MEL-93(DX6) | 703 ± 19 |
| Hs294T | 381 ± 44 |
| Hs852T | 202 ± 16 |
| Hs939 | 619 ± 44 |
| T294 | 366 ± 15 |
| M40 | 787 ± 75 |
| RON | 457 ± 27 |
| BMCL | 118 ± 31 |
| A375 parent[b] | 392 ± 38 |
| A375 Met Mix[b] | 659 ± 22 |
| A375 M6[b] | 612 ± 48 |
| B16-F10 (mouse melanoma) | 510 ± 34 |

[a]Heparanase assay was carried out by the incubation of a Triton X-100 cell extract (2.4 × 10$^5$ cells) with PNDS-N[$^{14}$C]Ac-HS immobilized on agarose beads (4500 cpm) at 37° C. for 12 h. The details of experiment are described in the materials and methods section. The radioactivity released in the presence of heat inactivated enzymes was subtracted from the raw data.
[b]A375 Met Mix and A375 M6 cells derived from lung metastases of A375 parental cells in athymic nude mice possess highly spontaneous lung metastatic potential, while A375 parental cells have very low spontaneous metastatic potential.

Heparanase Activity in Sera from Tumor Bearing Hosts

Preparation of blood sera. Blood was withdrawn by venepuncture without anticoagulant and allowed to clot for 1 hr at 22° C. Samples were centrifuged at 4° C. for 10 min at 800×g and for 15 min at 1600×g. The resultant sera were divided into small aliquots and snap-frozen in liquid nitrogen, and then maintained at −80° C. until analyzed.

Assay of sera for heparanase. The serum was diluted 5-fold with 0.1M sodium acetate buffer, pH 6.0, containing 0.15M sodium chloride. Two hundred microliter aliquot of the diluted serum was mixed with 200 ul of radiolabeled solid phase substrate suspension (3,000 cpm, 10 ug) in the same buffer and incubated at 37° C. At various incubation periods the enzyme reaction was terminated by chilling to 4° C., and the reaction sample was mixed with 40 ul of 50% trichloroacetic acid. The mixture was incubated for 10 min at 4° C. and centrifuged at 9800×g for 5 min. A two hundred microliter aliquot of the supermatant was withdrawn, neutralized with 55 ul of 1.0N sodium hydroxide, and then mixed with 4 ml of Liquiscint (National Diagnostic). The radioactivity was measured by a Beckman LS 2800 liquid scintillation counter. There was a linear relationship between incubation time and enzyme reaction. The activity was reported as units per milliliter serum. One unit of activity refers to the amounts of enzyme that liberates 1 ug of HS per minute.

Figure 4:
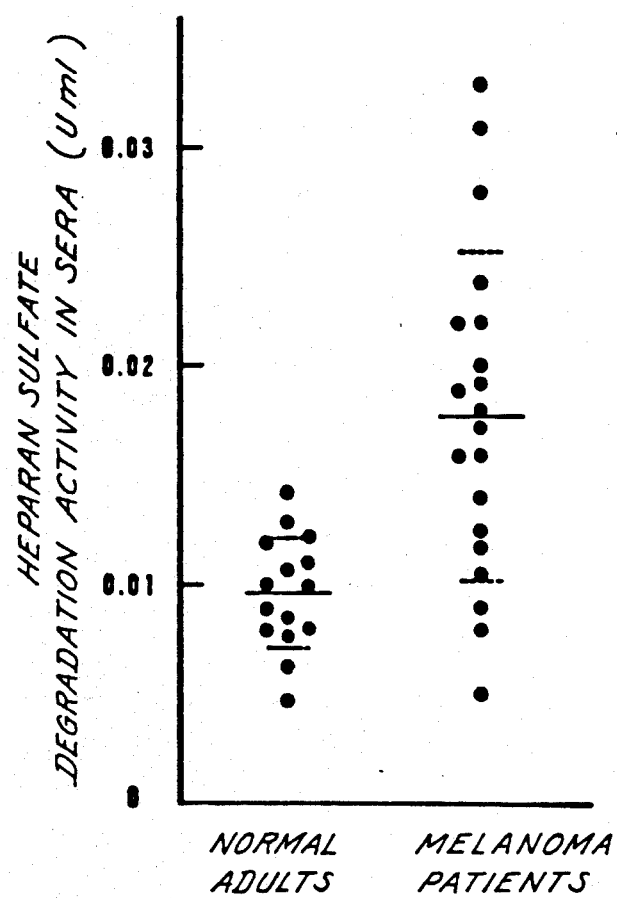
FIG. 4 show the levels of heparanase activity in the sera of controls and patients with malignant melanoma.

Heparanase activity in the sera from malignant melanoma patients. The sera from 20 melanoma patients at the various stages of the disease and from 15 normal adults were assayed for heparanase, and the results are shown in FIG. 4. The mean value and standard deviation of heparanase activity in the sera from melanoma patients and normal adults were 0.0177±0.0075 and 0.0096±0.0025 U/ml, respectively. The sera from some patients who have been treated by chemotherapy showed the normal levels of heparanase activity.

Figure 5:
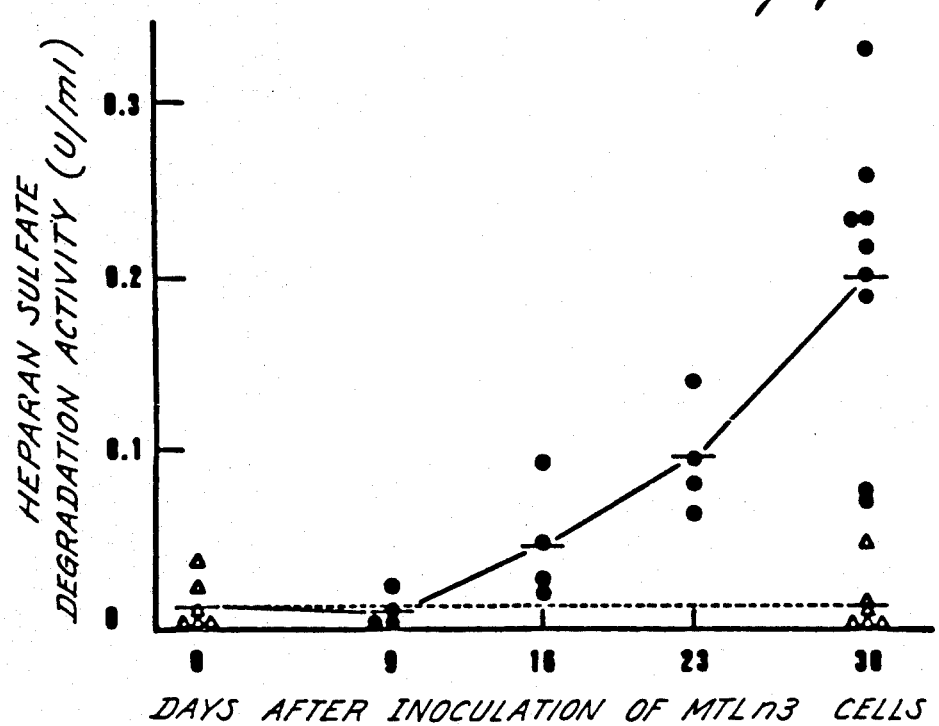
FIG. 5 shows levels of heparanase activity in sera of rats injected with a highly metastatic adenocarcinoma.
Figure 6:
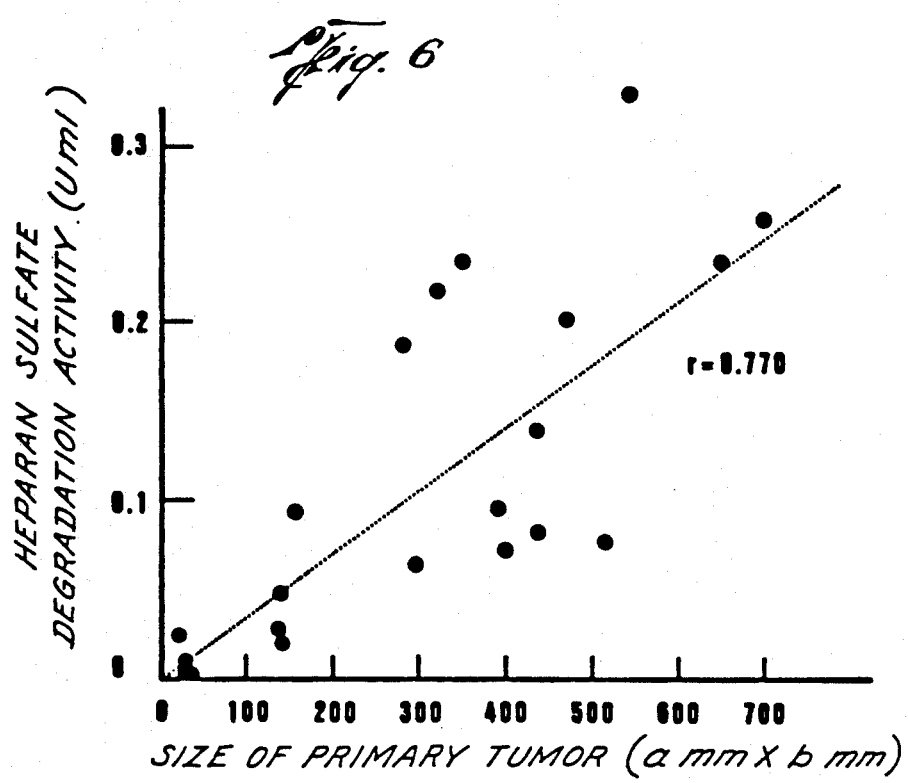
FIG. 6 shows the relationship between serum heparanase activity and the size of a primary metastatic tumor in rats.
Figure 7:
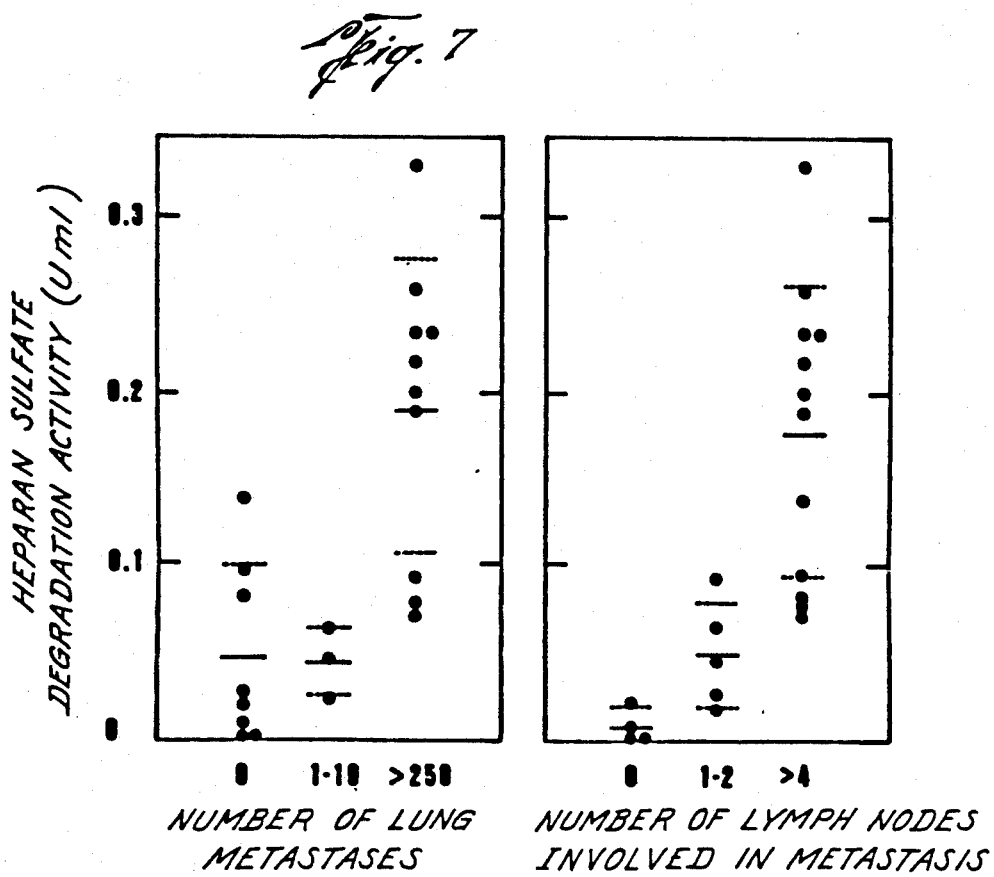
FIG. 7 shows the relationship between rat serum heparanase levels and numbers of metastases from a malignant tumor.

Heparanase activity in the sera from rats bearing 13762NF mammary adenocarcinoma. Highly metastatic mammary adenocarcinoma MTLn3 cells (1×10$^6$) were injected subcutaneously into the left inguinal mammary fat pad of age matched female F344 rats. Rats were sacrified at various periods post-injection, and the size of primary tumors, the number of lung metastases, and the serum heparanase activity were measured. The heparan sulfate degradative activities in sera increased with time after the subcutaneous inoculation of MTLn3 cells (FIG. 5). The activities in sera correlated with the sizes of the primary tumors (correlation coefficient r=0.770, FIG. 6). The sera from rats with large numbers of metastases in the lymph nodes and lungs demonstrated much higher heparanase activities than the sera from rats with few or no metastasis (FIG. 7).

Purification of melanoma heparanase. Melanoma cells (murine B16 melanoma subline B16-BL6 or human melanoma Hs 939 cells) were grown in a 1:1 mixture of DME/F12 medium supplemented with 5% heat-inactivated fetal bovine serum. Subconfluent cells were harvested by a treatment for 10 min with 2 mM EDTA in PBS and then washed twice in 0.14M NaCl, 10 mM Tris-HCl buffer, pH 7.2. The following steps were performed at 4° C. Cells ($2 \times 10^8$) were extracted in 30 ml of 50 mM Tris-HCl buffer, pH 7.2, containing 0.2% Triton X-100, 10 uM PMSF (buffer A) for 1 hr. The supernatant (approximately 1.5 mg protein/ml) was collected after centrifugation at $30,000 \times g$ for 30 min, and was loaded on a column of concanavalin A-Sepharose 4B ($2 \times 10$ cm) equilibrated with buffer A. After washing with 10 ml of buffer A, the absorbed material was eluted with 1M alpha-methyl-D-mannoside in buffer A. The eluents were filtered through a heparin-sepharose CL-6B column ($2 \times 10$ cm) equilibrated with 50 mM Tris HCl buffer, pH 7.2, containing 0.15M sodium chloride 0.2% Triton X-100. The column was washed with 100 ml of the same buffer and 100 ml of 0.15M sodium chloride 50 mM Tris-HCl, pH 7.2, and then heparin-bound proteins were eluted with a linear salt gradient (0.15M-1.2M sodium chloride). The heparanase active fractions were collected and dialyzed against 0.15M sodium chloride and 0.01M potassium phosphate, pH 6.0. After centrifugation at $50,000 \times g$ for 30 min, the supernatant was loaded on a hydroxylapatite column ($1.5 \times 45$ cm) equilibrated with 0.15M sodium chloride and 0.01M potassium phosphate, pH 6.0. Heparanase was eluted with a linear gradient of potassium phosphate (0.01M to 0.6M) in 0.15M sodium chloride, pH 6.0. The heparanase fractions were concentrated by ultrafiltration using YM-10 membranes, and were subjected to the further purification by Sepharose CL-6B gel filtration. The Sepharose CL-6B chromatography was performed in 0.15M sodium chloride, and 20 mM potassium phosphate, pH 6.0. Further chromatography, now with Sephadex G-150, was carried out in 0.5M sodium chloride and 25 mM Tris-HCl, pH 7.5. A single heparanase peak obtained from the Sephadex chromatography contained a glycoprotein of $M_r$ 96,000.

Properties of human melanoma heparanase. Melanoma heparanase is active between pH 5.5 and 7.5 and degrades heparan sulfate but not other glycosaminoglycans. Heparin and dextransulfate are potent inhibitors of melanoma heparanase.

TABLE 2

HEPARANASE SUSCEPTIBILITY AND HEPARANASE INHIBITORY ACTIVITY OF CHEMICALLY MODIFIED HEPARAN SULFATE AND HAPARIN

| Glycosaminoglycans | Degradation[1] | Inhibition of HS Degradation[2] |
|---|---|---|
| Heparan sulfate (HS) | + | − |
| N,O—Desulfated HS | + | − |
| N,O—Desulfated and N—acetylated HS | + | − |
| N—Desulfated HS | + | − |
| N—Desulfated and N—acetylated HS | + | − |
| Heparin | − | ++ |
| N,O—Desulfated heparin | − | − |
| N,O—Desulfated and N—acetylated heparin | ± | − |
| N—Desulfated heparin | − | − |
| N—Desulfated and N—acetylated heparin | ± | + |
| N—Desulfated and N—methylated heparin | − | − |
| Carboxyl reduced heparin | − | ± |

[1] $^3$H-labeled glycosaminoglycan was incubated with a cell extract (80 ug of protein) in 0.1 M sodium acetate buffer (pH 6.0) containing 0.15 M NaCl, 0.2% Triton X-100 and 0.05% NaN$_3$ for 6 hr at 37° C. in the presence of 20 mM D-saccharic acid 1,4-lactone (SAL) and was then subjected to high-speed gel-permeation chromatography. Percent of degradation was determined by measuring the decrease in area of the high $M_r$ half of the glycosaminoglycan peak (see FIG 2). +, more than 80%; ±, 5% to 15%; −, less than 5% (S.D. < 5.0%).
[2] Five micrograms of unlabeled glycosaminoglycan was added to the incubated mixture of $^3$H-labeled HS from bovine lung and a cell extract. Inhibition of HS degradation was determined by measuring the decrease in area of the high $M_r$ half of the HS peak. ++, more than 80% inhibition; +, 25-50% inhibition; ±, 5-25% inhibition; −, less than 5% inhibition (S.D. < 5%).

Changes may be made in the construction, operation and arrangement of the various parts, elements, steps and procedures described herein without departing from the concept and scope of the invention as defined in the following claims.

What is claimed is:

1. A method of producing a liquid-phase substrate which, upon hydrolysis by a glycosaminoglycan endoglycosidase, yields labeled products, and using said substrate to assay human glycosaminoglycan endoglycosidase, the method comprising the steps of;
   (a) labeling a glycosaminoglycan at one or more sites with a label yielding a detectable signal;
   (b) tagging the labeled glycosaminoglycan with a tag at a site on the glycosaminoglycan that has not been labeled wherein said tag has a binding affinity for a specific protein;
   (c) incubating the labeled and tagged glycosaminoglycan in a buffered aqueous solution with a human biological sample suspected of containing glycosaminoglycan endoglycosidase;
   (d) separating, using the specific protein, any labeled untagged products resulting from glycosaminoglycan endoglycosidase-induced hydrolysis of the labeled and tagged glycosaminoglycan substrate from tagged products and unaltered labeled and tagged glycosaminoglycan substrate; and
   (e) determining amounts of labeled untagged product, said amounts being proportional to glycosaminoglycan endoglycosidase levels in the human biological sample.

2. The method of claim 1 wherein the separating step involves use of an antibody raised to the tagging molecule or use of a binding protein which binds to the tagging molecule.

3. The method of claim 2 wherein the antibody or binding protein is coupled to a solid-phase support.

4. A method of producing a liquid-phase substrate which, upon hydrolysis by a heparin sulfate endoglycosidase, yields labeled products and using said substrate to assay human heparin sulfate endoglycosidase, the method comprising the steps of:
   (a) labeling heparan sulfate at one or more sites with a label yielding a detectable signal;
   (b) tagging the labeled heparan sulfate with a tag at a site on the heparan sulfate that has not been labeled wherein said tag has a binding affinity for a specific protein;

(c) incubating the labeled and tagged heparan sulfate in a buffered aqueous solution with a human biological sample suspected of containing heparan sulfate endoglycosidase;

(d) separating, using the specific protein, any labeled untagged products resulting from heparin-sulfate endoglycosidase-induced hydrolysis of the labeled and tagged heparan sulfate; and (e) determining amounts of labeled untagged product, said amounts being proportional to heparan sulfate endoglycosidase levels in the human biological sample.

5. The method of claim 4 wherein the separation is achieved by an antibody raised to the tag or by a binding protein which binds to the tag.

6. The method of claim 5 wherein the antibody or binding protein is coupled to a solid-phase support.

7. A method for producing a soluble glycosaminoglycan substrate comprising a label and a tag, the glycosaminoglycan substrate, upon hydrolysis by a glycosaminoglycan endoglycosidase, yielding soluble products comprising a label and soluble products comprising a tag, the soluble products comprising a tag and unhydrolyzed glycosaminoglycan substrate being extractable from solution upon exposure to a solid phase protein having binding affinity for the tag, the method comprising the steps of:

(a) labeling a glycosaminoglycan substrate for glycosaminoglycan endoglycosidase at one or more sites with a label which yields a detectable signal, said label not substantially impeding glycosaminoglycan endoglycosidase-induced hydrolysis of the glycosaminoglycan substrate;

(b) binding the labeled glycosaminoglycan substrate to a tag at a site on the glycosaminoglycan substrate that has not been labeled, the tag having affinity for a protein which may be attached to a solid matrix, said tag not substantially impeding glycosaminoglycan endoglycosidase-induced hydrolysis of glycosaminoglycan substrate.

8. A method for assaying a glycosaminoglycan endoglycosidase comprising the steps of:

(a) labeling a glycosaminoglycan substrate for glycosaminoglycan endoglycosidase at one or more sites with a label which yields a detectable signal, said label not substantially impeding glycosaminoglycan endoglycosidase-induced hydrolysis of the glycosaminoglycan substrate;

(b) binding the labeled glycosaminoglycan substrate to a tag at a site on the labeled glycosaminoglycan substrate that has not been labeled, the tag having affinity for a protein which may be attached to a solid matrix, said tagging molecule not substantially impeding glycosaminoglycan endoglycosidase-induced hydrolysis of the labeled and tagged glycosaminoglycan substrate;

(c) incubating the labeled and tagged glycosaminoglycan substrate with a buffered aqueous solution comprising a human biological sample suspected of containing glycosaminoglycan endoglycosidase; and (d) separating glycosaminoglycan substrate and tagged products resulting from glycosaminoglycan endoglycosidase-induced hydrolysis from untagged labeled products resulting from the hydrolysis, said separation involving binding of glycosaminoglycan-bound tag to a protein having an affinity for the tag.

9. A method for producing a soluble heparan sulfate derivative comprising a label and a tag, the heparan sulfate derivative, upon hydrolysis by a heparanase, yielding soluble products comprising a label and soluble products comprising a tag, the soluble products comprising a tag being extractable from solution upon exposure to a solid phase protein having binding affinity for the tag, the method comprising the steps of:

(a) labeling a heparan sulfate substrate for heparanase at one or more sites with a label which yields a detectable signal said label not substantially impeding heparanase-induced hydrolysis of the heparan sulfate substrate;

(b) binding the labeled heparan sulfate substrate to a tag at a site on the heparan sulfate that has not been labeled, the tag having binding affinity for a protein which may be attached to a solid matrix, said tag not substantially impeding heparanase-induced hydrolysis of the heparan sulfate substrate.

10. A method for assaying a heparanase comprising the steps of:

(a) labeling a heparan sulfate substrate for heparanase at one or more sites with a label which yields a detectable signal said label not substantially impeding heparanase-induced hydrolysis of the heparan sulfate substrate;

(b) tagging the labeled heparan sulfate substrate with a tag at a site on the heparan sulfate that has not been labeled, the tag having binding affinity for a protein which may be attached to a solid matrix, said tag not substantially impeding heparanase-induced hydrolysis of the heparan substrate;

(c) incubating the labeled and tagged heparan sulfate substrate with a buffered aqueous solution comprising a human biological sample suspected of containing heparanase; and (d) separating heparan sulfate substrate and tagged products resulting from heparanase-induced hydrolysis from untagged labeled products resulting from the hydrolysis, said separation involving binding of tagged molecules to a protein having a binding affinity for the tag.

11. The method of claim 8 or 10 wherein the protein having a binding affinity for the bound tag is affixed to a solid matrix.

12. A kit useful for the detection of glycosaminoglycan endoglycosidase in a sample which comprises:
a carrier being compartmentalized to receive one or more container means in close confinement therein;
a first container means comprising substrate for glycosaminoglycan endoglycosidase, said substrate bearing a tag and a detectable label;
a second container means comprising a protein which has specific binding affinity for the tag of the substrate.

13. The kit of claim 12 wherein said protein is a monoclonal antibody.

14. The kit of claim 13 wherein said monoclonal antibody in said first container means is immobilized on said container means.

15. The kit of claim 12 wherein said detectable label is a radiolabel, an enzyme label, a fluorescent label or a chromophore.

16. The kit of claim 12 wherein said protein is an antibody.

17. The kit of claim 12 which also comprises a multiplicity of container means with different amounts of glycosaminoglycan endoglycosidase antigen.

18. The kit of claim 12 which also comprises a multiplicity of container means with different amounts of detectable label.

19. The kit of claim 12 wherein said container means are tubes.

20. The method of claims 1, 4, 7 or 8 wherein the label is a radioisotope, enzyme, chromophore or fluorescein.

21. The method of claims 1, 4, 7 or 8 wherein the label is carbon 14, iodine 125 or tridium.

22. The method of claims 1, 4, 7 or 8 wherein the tag is biotin, a protein or a peptide.

* * * * *

UNITED STATES PATENT AND TRADEMARK OFFICE
CERTIFICATE OF CORRECTION

PATENT NO. : 4,859,581
DATED : August 22, 1989
INVENTOR(S) : Nicolson et al.

It is certified that error appears in the above—identified patent and that said Letters Patent is hereby corrected as shown below:

In claim 4, line 59, column 22 delete the word "heparin" and insert the word --heparan--.

In claim 4, line 61, column 22 delete the word "heparin" and insert the word --heparan--.

In claim 4, line 6, column 23 delete the word "heparin" and insert the word --heparan--.

In claim 10(b), line 32, column 24 insert the word --sulfate-- between the words "heparan" and "substrate".

Signed and Sealed this

Twenty-eighth Day of April, 1992

*Attest:*

HARRY F. MANBECK, JR.

*Attesting Officer*  *Commissioner of Patents and Trademarks*